US007329241B2

(12) United States Patent
Horvath et al.

(10) Patent No.: US 7,329,241 B2
(45) Date of Patent: Feb. 12, 2008

(54) DRUG DELIVERY SYSTEM FOR ADMINISTERING AN ADJUSTABLE PRESET DOSE

(75) Inventors: Michael W. Horvath, Cottage Grove, MN (US); David F. Jensen, Sunnyvale, CA (US); Mark R. Sponsel, San Jose, CA (US); Joseph P. Rossi, Rail Road Flat, CA (US); Gregory D. Malone, Encinitas, CA (US)

(73) Assignee: Valeant Pharmaceuticals North America, Costa Mesa, CA (US)

( * ) Notice: Subject to any disclaimer, the term of this patent is extended or adjusted under 35 U.S.C. 154(b) by 572 days.

(21) Appl. No.: 10/367,626

(22) Filed: Feb. 14, 2003

(65) Prior Publication Data

US 2004/0162528 A1 Aug. 19, 2004

(51) Int. Cl.
*A61M 5/00* (2006.01)
(52) U.S. Cl. .................................... 604/208
(58) Field of Classification Search ............ 604/207, 604/208, 209, 210, 211, 212–224, 187
See application file for complete search history.

(56) References Cited

U.S. PATENT DOCUMENTS

| 2,648,334 | A | * | 8/1953 | Brown et al. ............... 604/205 |
| 2,725,877 | A | * | 12/1955 | Reiter et al. ................ 604/135 |
| 4,073,321 | A | * | 2/1978 | Moskowitz ................... 141/27 |
| 4,936,833 | A | * | 6/1990 | Sams ......................... 604/232 |
| 5,115,816 | A | | 5/1992 | Lee |
| 5,951,526 | A | * | 9/1999 | Korisch et al. ............. 604/208 |
| 5,964,736 | A | * | 10/1999 | Lane .......................... 604/220 |
| 6,579,269 | B1 | * | 6/2003 | Kleyman .................... 604/207 |
| 6,770,056 | B2 | * | 8/2004 | Price et al. ................. 604/246 |

FOREIGN PATENT DOCUMENTS

EP 0 904 792 A2 3/1999
WO WO 95/01198 1/1995

* cited by examiner

*Primary Examiner*—Manuel Mendez
(74) *Attorney, Agent, or Firm*—McDermott Will & Emery LLP (57) ABSTRACT

An embodiment of the present invention provides an apparatus for setting a dose of a drug in a syringe having a plunger, comprising an outer housing and an inner housing adapted for encircling the syringe, such that the inner housing is positioned within the outer housing to set the dose of the drug. In an embodiment, the apparatus further comprises a dosage indicator disposed on the inner housing and the outer housing further comprises an opening for viewing the dosage indicator.

53 Claims, 13 Drawing Sheets

DRUG DELIVERY SYSTEM FOR ADMINISTERING AN ADJUSTABLE PRESET DOSE

CROSS-REFERENCE TO RELATED APPLICATION

The present application is filed concurrently herewith U.S. patent application Ser. No. 10/367,598 and entitled "APPLICATOR TIP FOR A DRUG DELIVERY SYSTEM," the disclosure of which application is hereby incorporated by reference.

BACKGROUND OF THE INVENTION

1. Field of the Invention

The present invention relates to systems for delivering a dosage of a drug to a patient.

2. Background

Drugs are often intended to be administered to a patient by an at home health care provider. Because of various factors, however, different amounts of the drug must be administered to different patients. Such factors can include, for example, the size and weight of the patient, the age of the patient, the sex of the patient, whether the patient is a child or an adult, etc. Currently, in order to administer the proper dose to the patient, drug delivery devices typically require that the device is manufactured such that the entire volume is metered to deliver the desired dose of the drug, or the at home health care provider must adjust the volume to be delivered, thereby adjusting the dose themselves. Both of these options, however, have certain inherent drawbacks.

In the former case, the manufacturer is required to make several versions of a device, with each version including a different volume (usually incremental) of the drug. Further, because several different versions of the device are required, both the distributor of the drug and the pharmacist are required to use more "shelf space" by keeping an inventory of the various devices containing different amounts of the drug.

In the latter case, it is more likely (as compared to a pharmacist) that the at home health care provider might make an error in setting the proper dosage. This could be especially important if the patient requires an immediate injection of the drug (due to a medical emergency).

Figure 1:
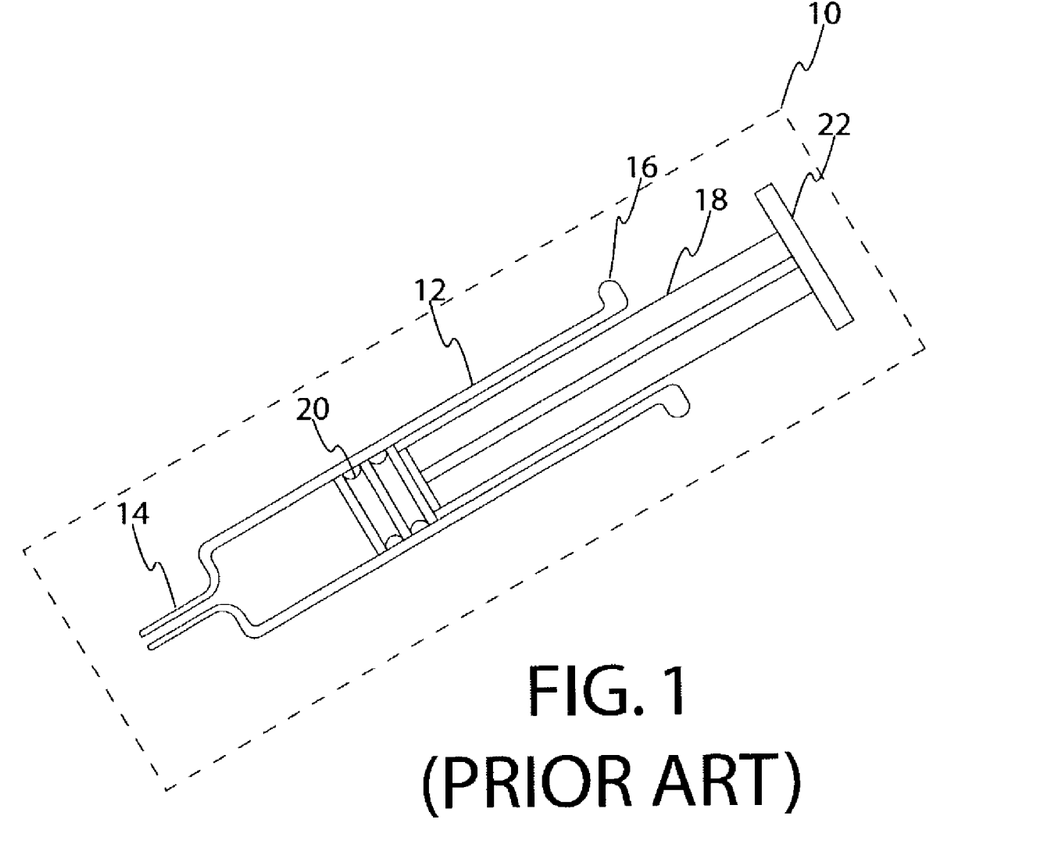
FIG. 1, described above, is a cross section view of a conventional syringe.

A cross section view of an example of a conventional syringe 10 is shown in FIG. 1. The syringe 10 typically comprises a barrel 12 having a proximal end designed for receiving a plunger 18 and a distal end designed for attaching an applicator tip to expel the drug into the patient. Before administration of a medicine, the drug formulation is metered into the barrel 12 of the syringe 10 to a predetermined volume. Next, the plunger 18 is inserted into the proximal end of the barrel 12. The drug can then be expelled by pushing the plunger 18 toward the distal end of the barrel 12.

As shown in FIG. 1, the proximal end of the barrel 12 can further comprise a flange 16, and the distal end of the barrel 12 can further comprise a syringe tip 14. Typically, the plunger 18 further comprises a shaft having a disk-shaped flange 22 located on its proximal end and a stopper 20, usually made of a rubber material, attached to its distal end. The shaft and the disk-shaped flange 22 are often formed from a single piece of material such as either glass or plastic. The stopper 20 is usually attached to the shaft of the plunger 18 by providing a threaded tip (not shown) to the end of the shaft for screwing into the stopper 20.

There is a need for drug delivery systems for the treatment of patients who experience epileptic seizures. Typically, patients who suffer increased and intermittent seizure activity due to epilepsy are treated via a rectal drug delivery device that administers a pre-set dose of a drug such as diazepam in a gel form. As discussed above, however, there is a need for a system that employs a conventional syringe for delivering an adjustable pre-set dosage of a drug.

BRIEF SUMMARY OF THE INVENTION

One embodiment of the present invention provides an apparatus for setting a dose of a drug in a syringe having a plunger, comprising an outer housing and an inner housing adapted for encircling the syringe, such that the inner housing is positioned within the outer housing to set the dose of the drug. In an embodiment, a dosage indicator disposed on the inner housing and the outer housing further comprises an opening for viewing the dosage indicator.

In another embodiment of the present invention, a locking assembly is connected to the inner housing and the outer housing for fixing the relative positions of the inner housing and the outer housing such that the dosage indicator is viewable through the opening in the outer housing.

In a further embodiment, a dosage indicator is disposed on the outer housing and provides a predetermined number of dosages of the drug in increments ranging from approximately 0.25 ml to approximately 5 ml. In another embodiment, a dosage indicator provides a predetermined number of dosages of the drug in increments ranging from approximately 0.5 mg to approximately 10 mg.

In an embodiment, a limiter attached to either the inner or the outer housing for fixing at least one distance that the plunger can move within the syringe. In another embodiment, the plunger is substantially cylindrical in shape.

In yet another embodiment, a grip connected to either or both the inner and outer housing to adjust the amount of and/or deliver the dosage to a patient. In another embodiment, a nozzle is attached to the inner housing for the dispensing of the drug and has a material disposed on the exterior of the nozzle. In one embodiment, the material comprises a lubricious material, such as a polymer material containing polytetrafluoroethylene. In an embodiment, a removable covering is attached to either the nozzle or the syringe.

In an embodiment, the outer housing comprises two portions that are substantially cylindrical in shape. In another embodiment, threadings are disposed on the exterior of the inner housing and the interior of the outer housing, such that the threadings on the inner and outer housing are slidably disposed within each other and the relative axial positions of the inner and outer housings are adjustable by rotation of the outer housing relative to the inner housing. In one embodiment, the threadings on the inner and outer housings are predetermined such that a desired predetermined dosage corresponds to a predetermined amount of rotation of the outer housing relative to the inner housing.

In yet another embodiment, locking assemblies are attached to the inner housing, the outer housing and/or the syringe for fixing the relative positions of the syringe and the inner housing. In one embodiment, the drug comprises an anti-seizure medication such as diazepam.

DETAILED DESCRIPTION OF THE INVENTION

Reference is now made to FIGS. 2-13, which illustrate pictorially various embodiments of the invention.

Figure 2:
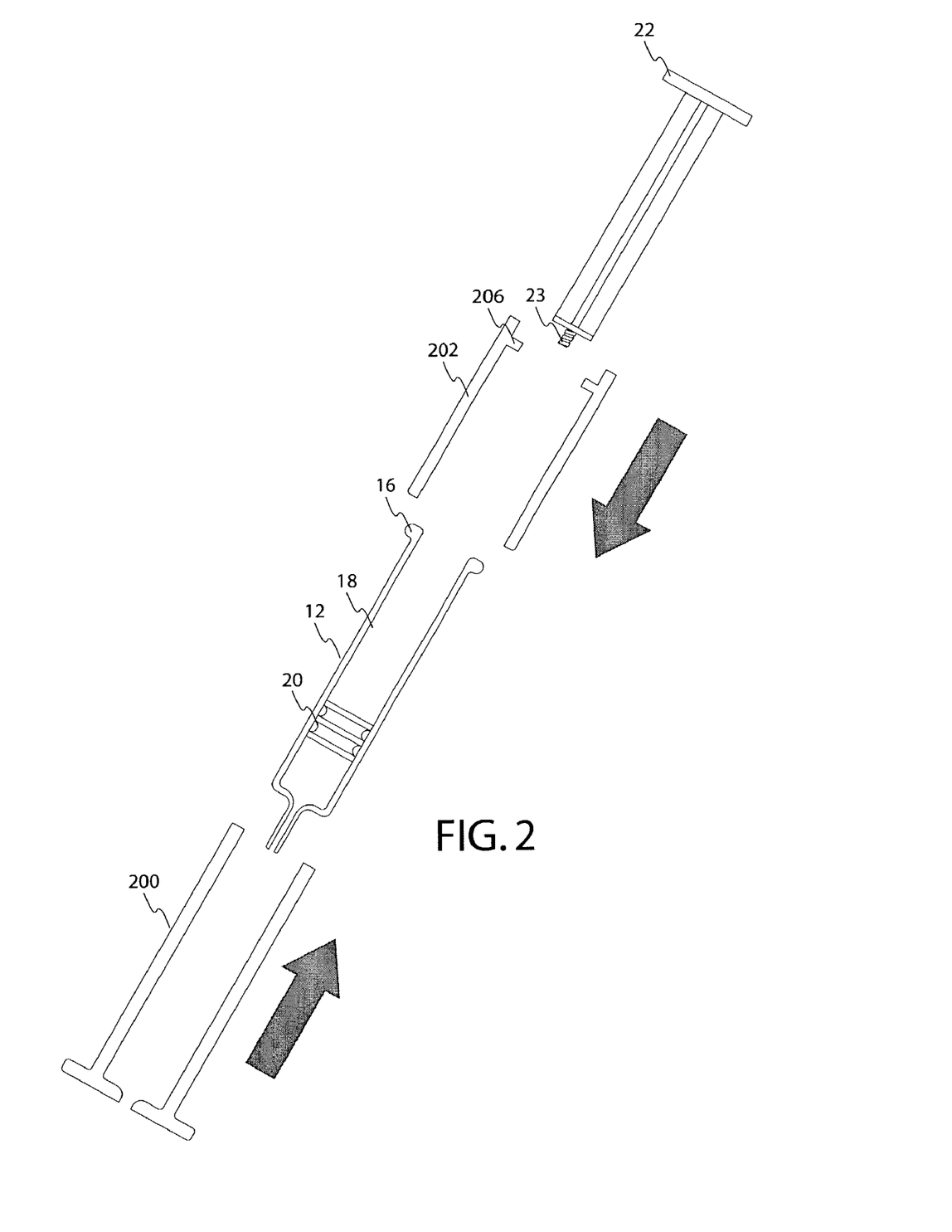
FIG. 2 is a cross section view of a simplified embodiment of the drug delivery system of the present invention.

FIG. 2 shows a cross section view of a simplified embodiment of the drug delivery system of the present invention. As shown in FIG. 2, in one embodiment the drug delivery system comprises an inner housing 200 and an outer housing 202 for use with a conventional syringe 10 as illustrated in FIG. 1. Generally, the drug delivery system of the present invention limits the axial movement of the plunger 18 of the syringe 10, thereby fixing the dose of the drug that can be administered. To accomplish this, in one example, the syringe 10 is inserted into the inner housing 200, which is inserted into the outer housing 202. In this embodiment the inner housing 200 and the outer housing 202 can be concentric tubes whereby the inner housing 200 is slidably disposed within the outer housing 202. The outer housing 202 is designed to limit the axial motion of the plunger by stopping the disk-shaped flange 22 on the proximal end of the plunger 18, thereby setting the amount of drug that can be delivered.

As shown in FIG. 2, a mechanism can be added to secure the position of the syringe 10. During assembly the syringe 10 filled with a drug formulation is disposed within the inner housing 200, which is inserted into the outer housing 202. The outer housing 202 comprises a plunger limiter 306. The flange 206 acts as a limit for the distance that the plunger 18 can be pushed into the barrel 12. The drug delivery system is then ready to be packed for delivery to a distributor or a dispenser, such as a pharmacist. In order to adjust the proper volume of the drug, the pharmacist can manipulate the outer housing 202 relative to the inner housing 200 by grasping the inner housing 200 and sliding the outer housing 202 up and down.

Figures 3A, 3B, 3C:
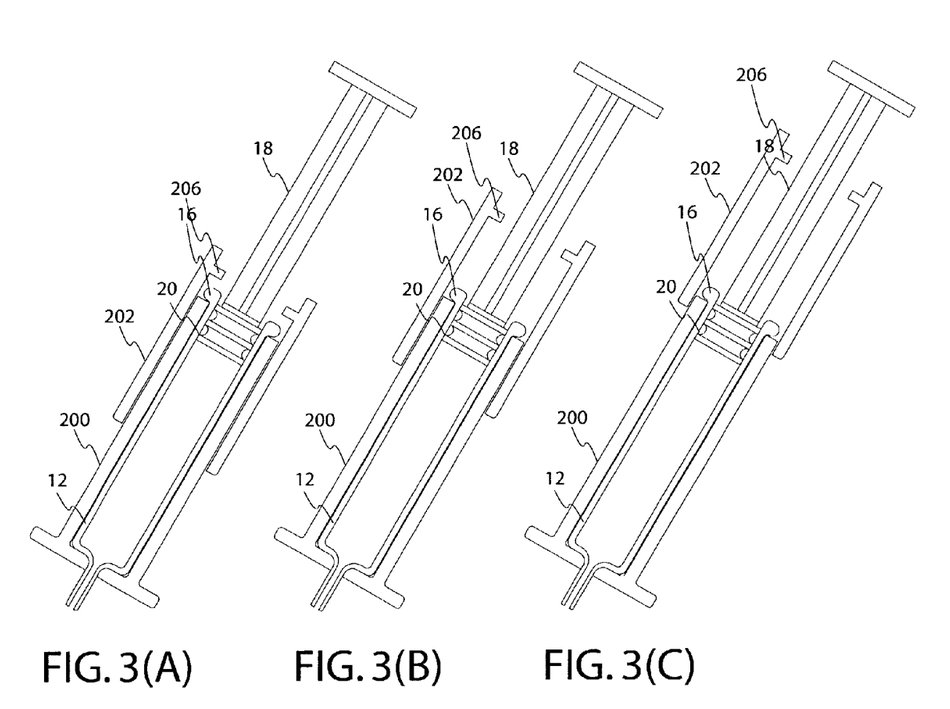
FIGS. 3(A)-(C) are cross section views of the embodiment of FIG. 2 illustrating various dosage amounts.

FIGS. 3(A)-(C) are cross section views of the embodiment of FIG. 2 illustrating various dosage amounts. In particular, three example settings of the drug delivery system of the present invention are illustrated in FIGS. 3(A)-(C). As shown in FIGS. 3(A)-(C), the setting of the inner housing 200 in relation to the outer housing 202 represent a "maximum", an "intermediate" and a "minimum" amount of drug that is to be administered to the patient. In FIG. 3(A), because the outer housing 202 is covering most of the inner housing 200 in an axial direction, the plunger 18 is allowed to fully depress into the barrel 12 of the syringe 10, thus delivering a maximum amount of the drug. In FIG. 3(C), because the outer housing 202 is covering the least of the inner housing 200 in an axial direction, the plunger 18 is only slightly allowed to depress into the barrel 12 of the syringe 10, thus delivering a minimum amount of the drug. In FIG. 3(B), the outer housing 202 is shown covering an intermediate portion [compared to FIGS. 3(A) and 3(C)] of the inner housing 200 in an axial direction. Therefore, because the plunger 18 is allowed to partially depress into the barrel 12 of the syringe 10, an intermediate amount of the drug can be delivered.

Figures 4A, 4B:
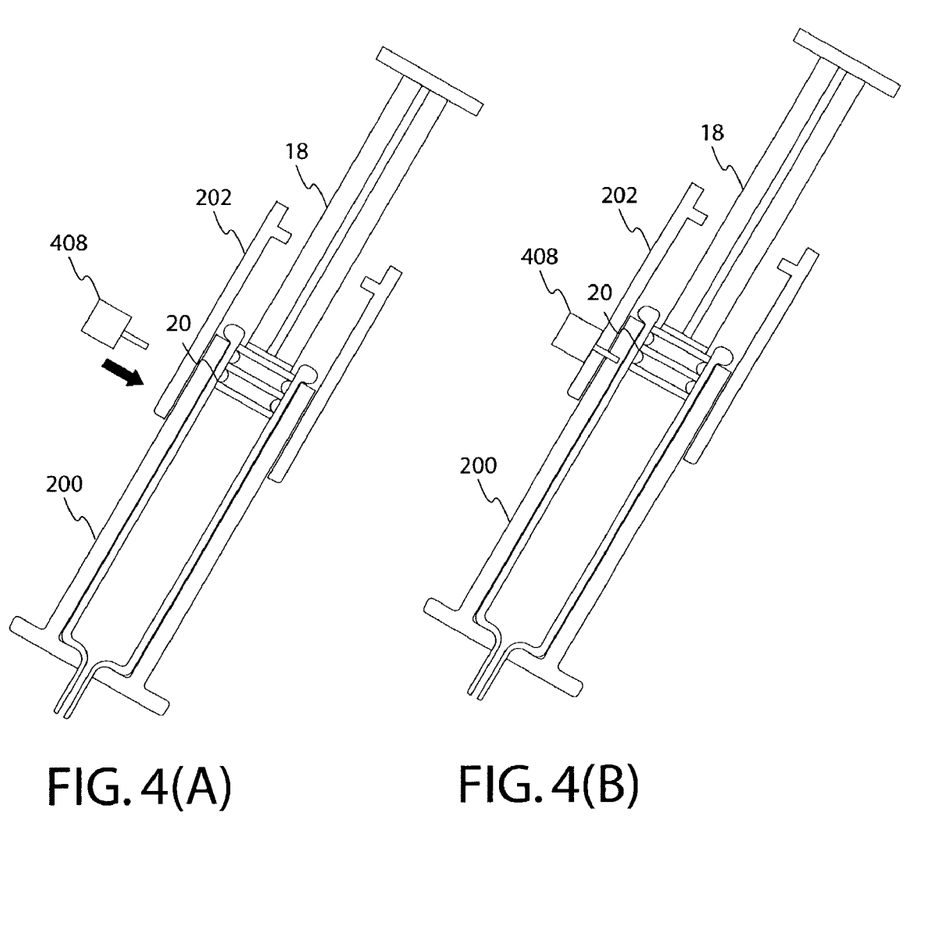
FIGS. 4(A)-(B) are cross section views of the embodiment of FIG. 2 illustrating a locking assembly.

FIGS. 4(A)-(B) are cross section views of the embodiment of FIG. 2 illustrating a locking assembly. As shown in FIGS. 4(A)-(B), once the volume of the drug is set for the drug delivery system, the position of the outer housing 202 relative to the inner housing 200 can be fixed by an intermediary with a locking assembly 408. In one embodiment, the locking assembly comprises a plastic or metal rod that is inserted through both the inner housing 200 and the outer housing 202. The intermediary can then repackage the drug delivery system for distribution to the end user.

Figures 5A, 5B:
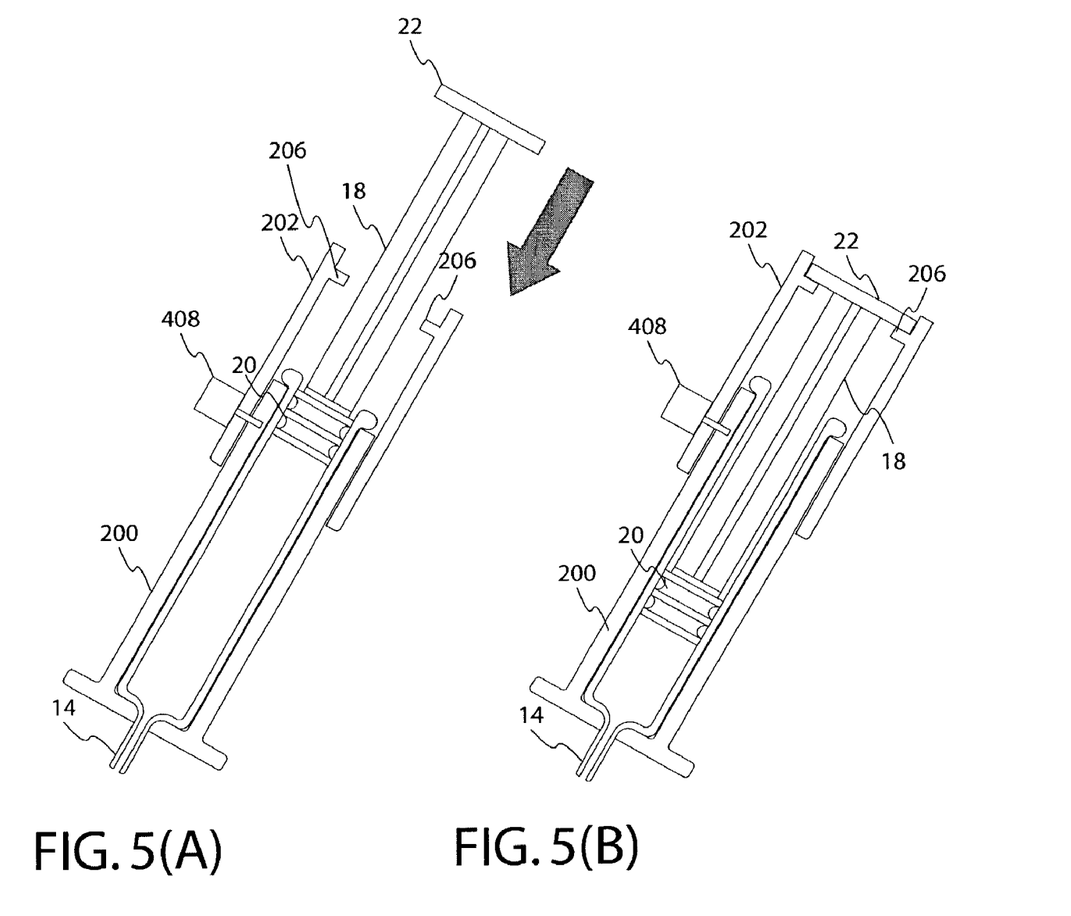
FIGS. 5(A)-(B) are cross section views of the embodiment of FIG. 2 illustrating the administration of a dose.

FIGS. 5(A)-(B) are cross section views of the embodiment of FIG. 2 illustrating the administration of a dose. As shown in FIGS. 5(A)-(B), once the dosage of the device has been properly set, the end user can administer the drug by depressing the plunger 18 until the disk-shaped flange 22 on the plunger 18 reaches the plunger flange 206 on the outer housing 202.

Figure 6:
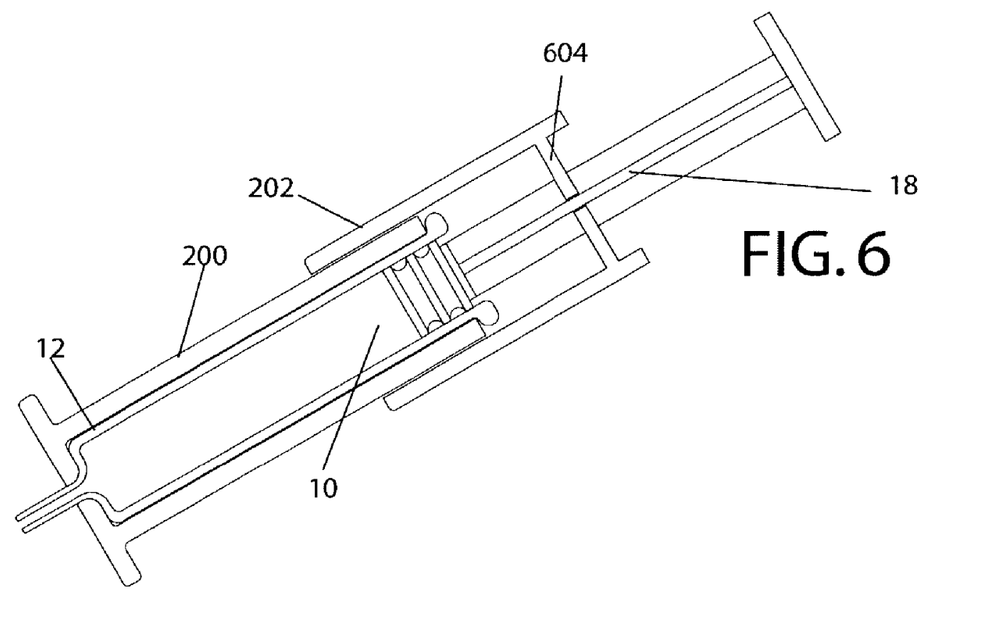
FIG. 6 is a cross section view of the embodiment of FIG. 2 comprising an apparatus to further secure the plunger.
Figure 7A:
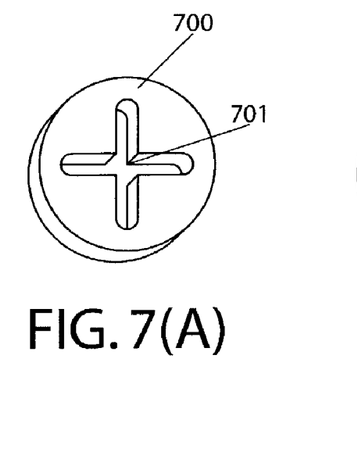
FIGS. 7(A)-(C) show perspective views of the plunger limiter in various embodiments of the drug delivery system of the present invention.
Figure 7B:
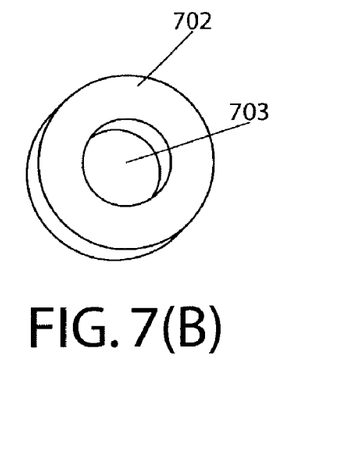
Figure 7C:
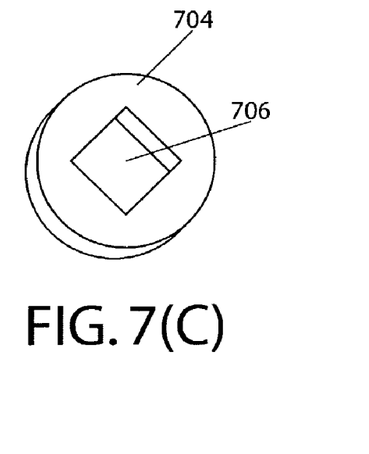

FIG. 6 is a cross section view of the embodiment of FIG. 2 that comprises an apparatus to further secure the plunger. FIGS. 7(A)-(C) show perspective views of the plunger limiter in various embodiments of the drug delivery system of the present invention. In particular, it is desirable to prevent the plunger 18 from being removed from the barrel 12 either accidentally or by tampering. In this embodiment, the possibility of tampering or accidental removal can be reduced by adding a plunger limiter, either to the inner housing 200 or the outer housing 202, or to both housings 200, 202. In this embodiment, the plunger 18 is of conventional design and therefore, comprises an "plus-sign" shape when viewed from a top cross section view. FIG. 7(A) shows a cross section view of the plunger limiter 700. As shown in FIG. 7(A), the plunger limiter 700 comprises a "plus-sign" shaped aperture 701 that is designed to loosely fit the cross section shape of a conventional plunger 18.

FIG. 6 illustrates a cross section view of an embodiment where the outer housing 202 comprises a plunger limiter 604 located on the proximal end of the outer housing 202. In the embodiment of FIG. 6, because there is not a plunger flange 206, the plunger limiter 604 acts as a bi-directional limiter for the position of the plunger 18.

As discussed above, while a conventional plunger has a "plus-sign" shape, other embodiments of the plunger limiter and plunger may be employed. For example, FIG. 7(B) shows an embodiment of the plunger limiter 702 that has a circular opening 703. In this embodiment, the shaft of the plunger 18 will also be a circular shape to allow the plunger 18 to travel easily through the circular opening 703 located within the barrel 12. In another example, FIG. 7(C) shows an embodiment of the plunger limiter 704 that has a square shaped opening 706. In this embodiment, the shaft of the plunger 18 will also be a square shape that is designed to fit within the square shaped opening 706. Other shapes are possible for the opening in the plunger limiter of the present invention.

Figure 8:
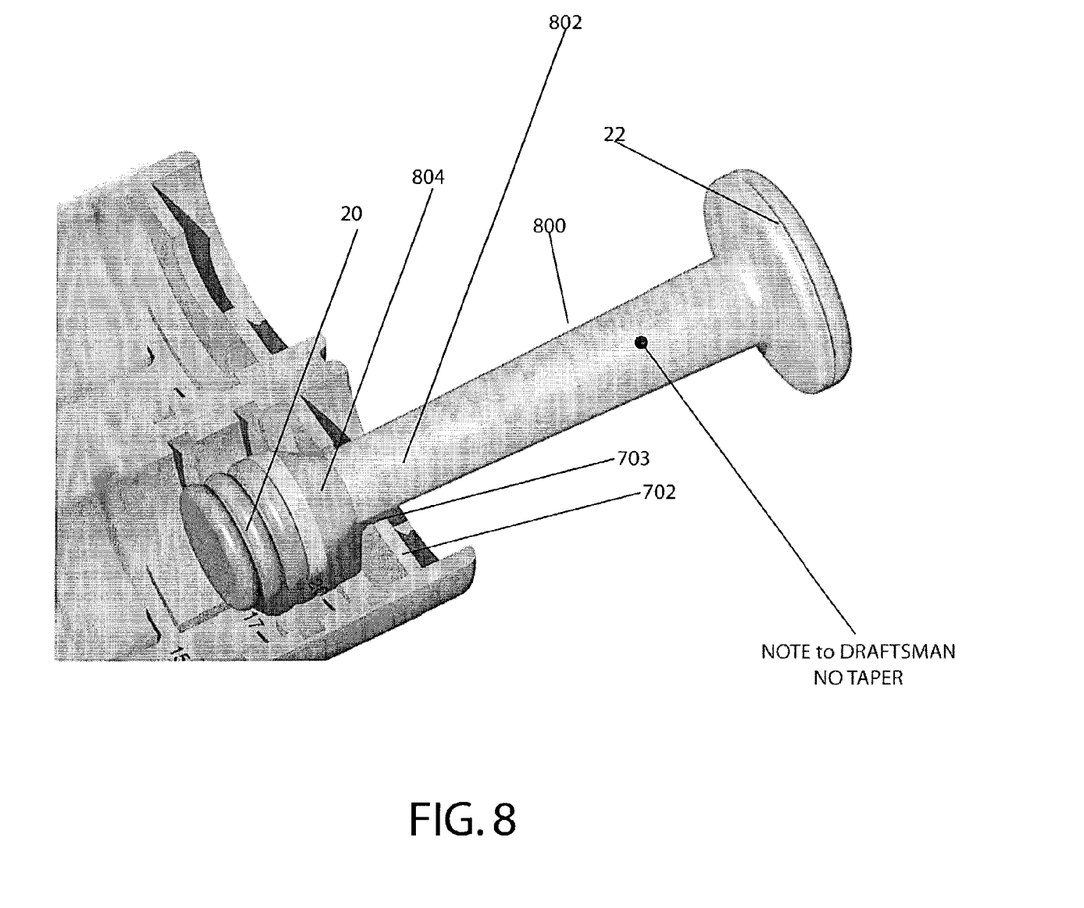
FIG. 8 is a perspective view of an embodiment of the plunger and outer housing of the drug delivery system of the present invention.

FIG. 8 is a perspective view of an embodiment of a plunger and outer housing of the drug delivery system of the present invention. FIG. 8 shows an embodiment a plunger 800 that is generally cylindrical in shape. In this embodiment, the plunger 800 is comprised of two portions, a proximal portion 802 and a distal portion 804. In this embodiment, the proximal portion 802 is generally cylindrical in shape and the distal portion 804 is generally tapered in shape. In this example, the distal portion 804, which is further connected to a conventional stopper 20 and the proximal portion 802 is connected to a disk-shaped flange 22. The plunger limiter 702 is the same as that described above in FIG. 7(B). In this embodiment, the circular opening 703 is designed with a smaller diameter than the diameter of the distal portion 804 of the plunger 800. Thus, when the plunger 800 is pulled out of the drug delivery system, the tapering of the distal portion 804 near the stopper 20 helps to prevent the accidental removal of the plunger 800.

Figures 9A, 9B:
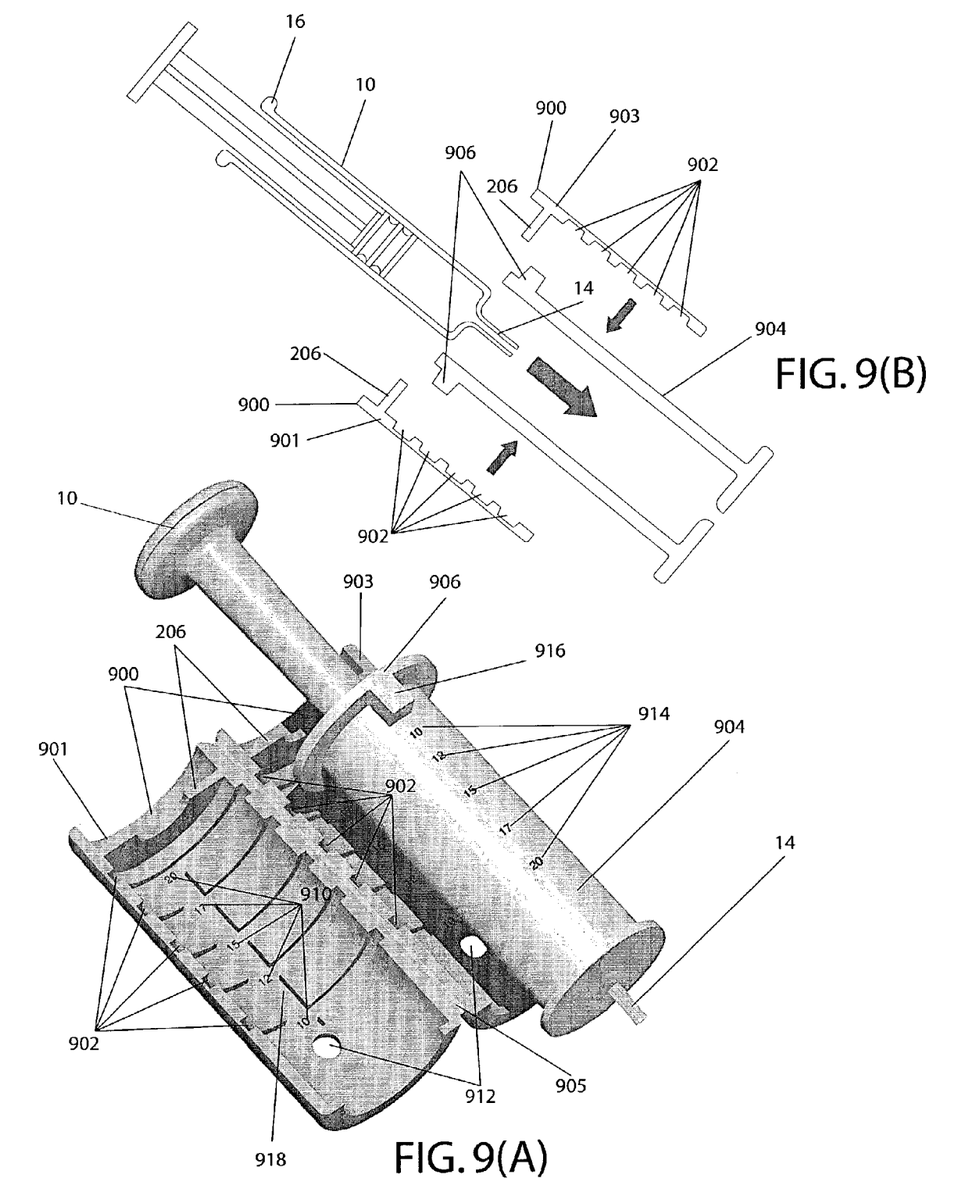
FIG. 9(A) is a perspective view and FIG. 9(B) is a cross section view of another embodiment of the drug delivery system of the present invention.

FIG. 9(A) is a perspective view and FIG. 9(B) is a cross section view of another embodiment of the drug delivery system of the present invention. In this embodiment, as compared with the embodiment of FIG. 2 where the two housings 200, 202 do not slide, the relative axial positions of inner housing 904 and outer housing 900 can be adjusted. In this embodiment, the outer housing 900 comprises two "clam shell" portions. Each portion 901, 903 is cylindrical in shape and, in one embodiment, 901, 903 are one continuous structure joined at seam 905. After assembly, the two housings 900, 904 are joined to form a hollow cylinder similar to the outer housing 202 described above for the embodiment of FIG. 2. Located on the interior of each portion 901, 903 of the outer housing 900 are a series of semicircular grooves 902. Thus, when the two portions 901, 903 are assembled to form a cylindrical shape the grooves 902 comprise a circular shape on the interior of the outer housing 900.

In the embodiment shown in FIG. 9, the inner housing 904 further comprises a positioning flange 906. The positioning flange 906 is a cylindrical shaped rim connected to the proximal end of the inner housing 904 and is designed to fit into any one of the grooves 902 of the outer housing 902. Each one of the grooves corresponds to a separate incremental volume of the drug. In one example, the axial position of the outer housing 900 relative to the inner housing 904 can be set to one of five distances that correspond to one of five different volumes of the drug that can be administered. In addition, after the positioning flange 906 is locked into one of the grooves 902, the dosage is set.

To make the presetting of the dose easier for the intermediary, a dose indicator 914 is located within the interior of the outer housing 902 that specifies each groove as to the volume of the drug it represents. In addition, a corresponding dose indicator 914 is located on the exterior of the inner housing 904. After assembly, the dosage setting can then be confirmed by the pharmacist through an opening 912 in the outer housing 900. In order to keep the opening 912 aligned with dose indicator 914, a key 916 on the positioning flange 906 is disposed within a matching recess 918 on the interior of the outer housing 900.

In another embodiment, the volume of the drug can be indicated and set by one or more lines (or other appropriate markings) located on the distal end of the inner housing 904 (not shown in FIG. 8). During assembly, an intermediary can locate the inner housing 904 within the outer housing 900 such that a line indicating the proper dosage is visible adjacent to the distal end of outer housing 900. In this embodiment, the dose indicator 914 and opening 912 are not necessary features.

Figure 10A:
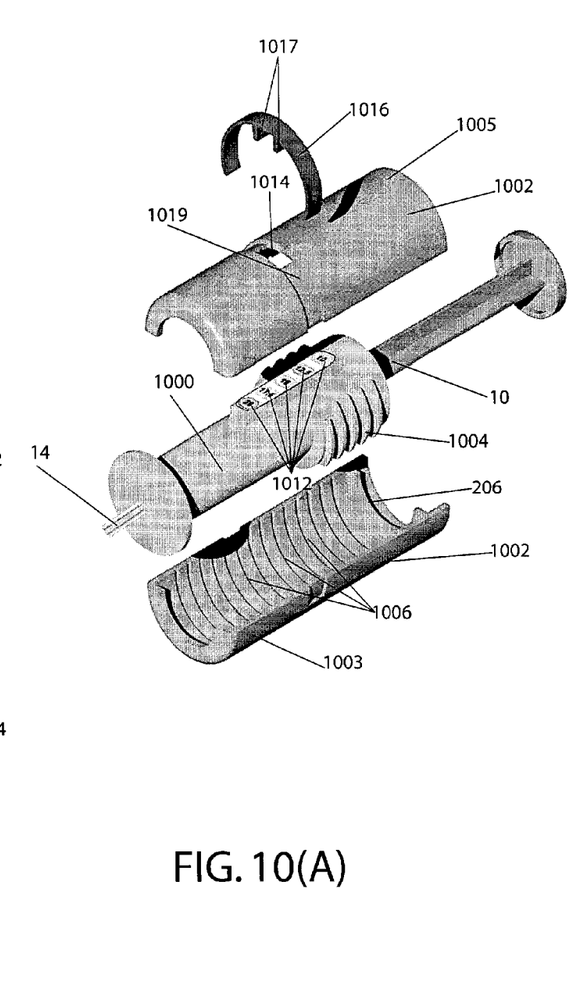
FIGS. 10(A)-(C) are perspective views of another embodiment of the drug delivery system of the present invention.
Figure 10B:
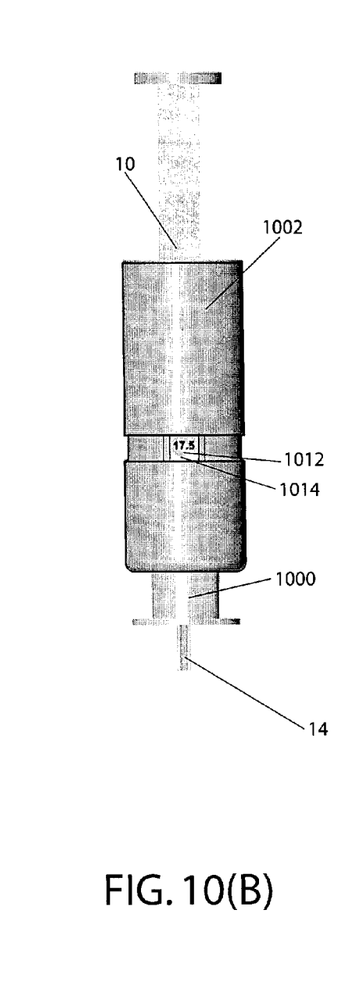
Figure 10C:
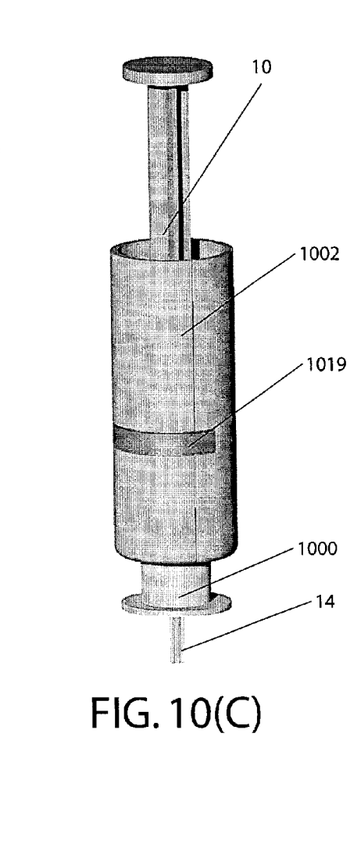
Figure 11A:
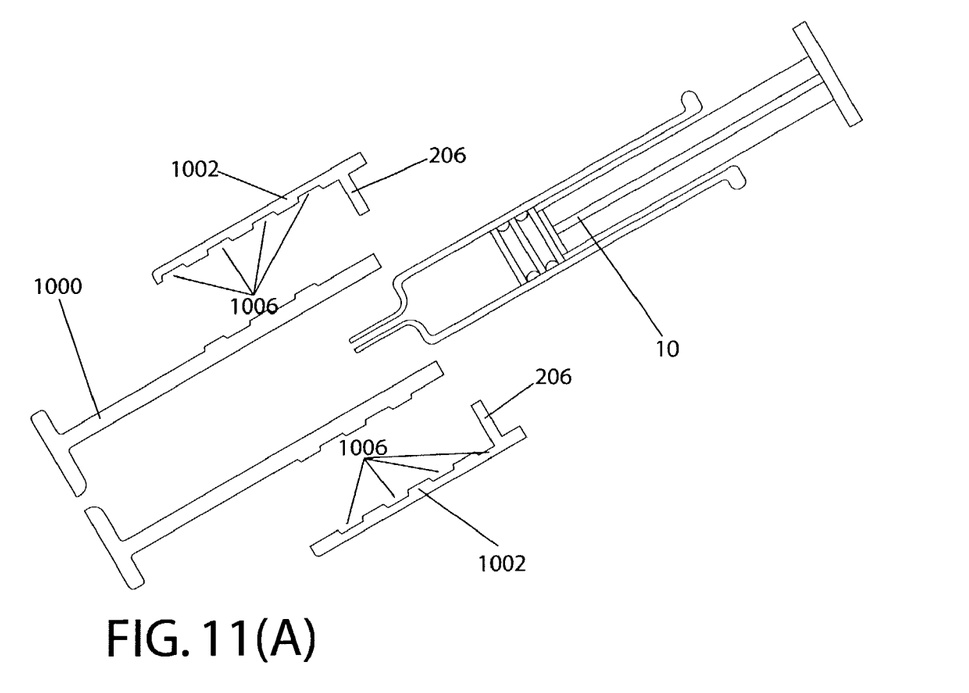
FIGS. 11(A)-(B) are cross section views of the embodiment of FIGS. 10(A)-(C) the drug delivery system of the present invention.
Figure 11B:
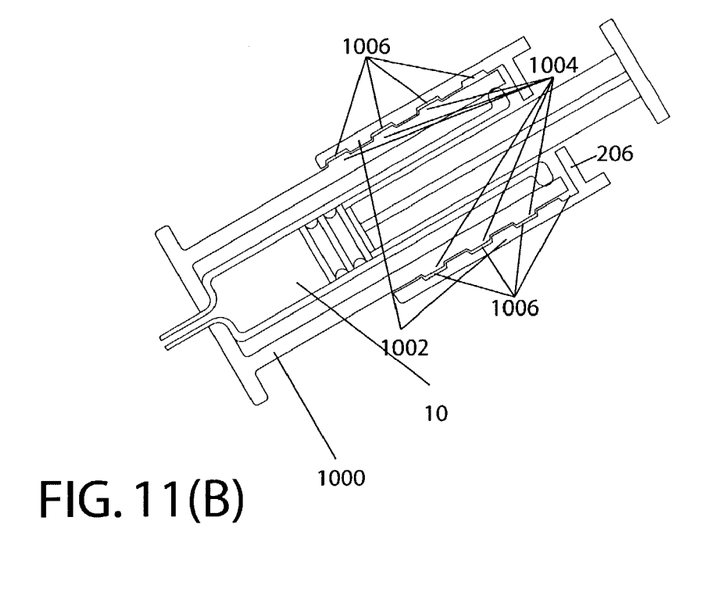

FIGS. 10(A)-(C) are perspective views and FIGS. 11(A)-(B) are cross section views of another embodiment of the drug delivery system of the present invention. In this embodiment, the drug delivery system comprises an inner housing 1000 and an outer housing 1002. In addition, the inner housing 1000 further comprises outer threading 1004 disposed on the exterior of the inner housing 1000. The outer housing 1002 further comprises two "clam shell" portions 1003, 1005, and an inner threading 1006 disposed on the interior of the outer housing 1002. In this embodiment, the outer threading 1004 comprises a "male" spiraling rim that protrudes from the inner housing 1000, and the inner threading 1006 comprises a "female" spiraling groove that corresponds to the "male" spiraling rim of the inner housing 1000. When the two portions 1003, 1005 of the outer housing 1002 are assembled, the outer threading 1004 of the inner housing 1000 is aligned within the inner threading 1006 of the outer housing 1002.

In this embodiment, the relative axial positions of the inner housing 1000 and the outer housing 1002 can be adjusted by rotating the outer housing 1002 relative to the inner housing 1000. In addition, a dose indicator 1012 is located on the exterior of the inner housing 1000, and a corresponding opening 1014 is located through the outer housing 1002 so that, after assembly, the pharmacist can visually confirm the dosage setting through the opening 1014 in the outer housing 1002.

In addition, the outer threading 1004 and the inner threading 1006 can be designed so that a certain number of complete rotations of the outer housing 1002 will correspond to a desired dosage of the drug. The system is designed to dispense a drug in variable pre-set volumes in increments of approximately 0.25 ml to approximately 10 ml. Further, the system is designed to dispense a drug in increments of weight ranging from approximately 0.5 mg to approximately 10 mg. In one example, the device is designed to deliver several pre-set volumes of a drug in the amounts of approximately 2.5 ml, 5 ml, 7.5 ml and 10 ml. In this example, setting the device for the 7.5 ml volume requires a single full rotation of the outer housing 1002, while the 5 ml volume requires two rotations and the 2.5 ml volume requires three rotations.

As shown in FIG. 10, in another embodiment, the drug delivery system can further comprise a locking assembly comprising a fastener 1016 that is semicircular in shape and having two protrusions 1017. During assembly, after the pharmacist chooses the proper dosage by rotating the outer housing 1002, the system can be locked by placing the fastener 1016 around a groove 1019 on the outer housing 1002 and pushing in so that the protrusions 1017 on the fastener fit around the dose indicator 1012. After the intermediary has set the dosage, a prescription label can be applied to the exterior of the outer housing 1002 that covers and effectively seals the fastener 1016 in position.

Figures 12A, 12B:
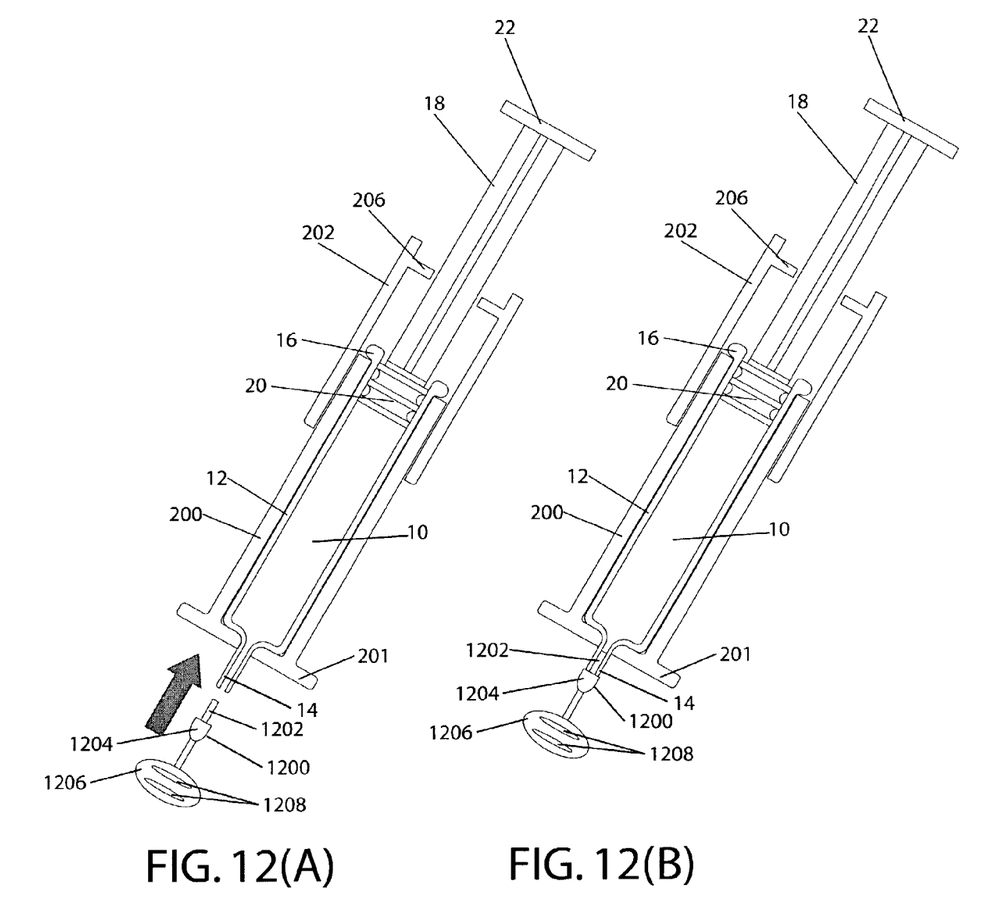
FIGS. 12(A)-(B) shows a cap assembly for use with an optional tip in an embodiment of the drug delivery system of the present invention.

FIGS. 12(A)-(B) show cross section views of an embodiment similar to that of the drug delivery system of FIG. 2, but comprising a cap assembly 1200 to further protect the device from both accidental discharge or tampering. As shown in FIG. 12, the cap assembly 1200 comprises a cylindrical shaped pin 1202 having a disk 1206 located on one end. The cap assembly also comprises a stopper 1204 disposed around the pin 1202. In one embodiment, the disk 1206 further comprises one or more ridges 1208. Typically, the pin 1202, the disk 1206 and the stopper 1204 can comprise a metallic or plastic material.

For use during shipping, a manufacturer inserts the cap assembly 1200 into a standard syringe 10 as shown in FIG. 12. During insertion of the cap assembly 1200, the ridges 1208 aid in grasping and inserting the assembly 1200 into the syringe 1200. After insertion, the pin 1202 is located within the syringe tip 14 on the syringe 10.

Figure 13:
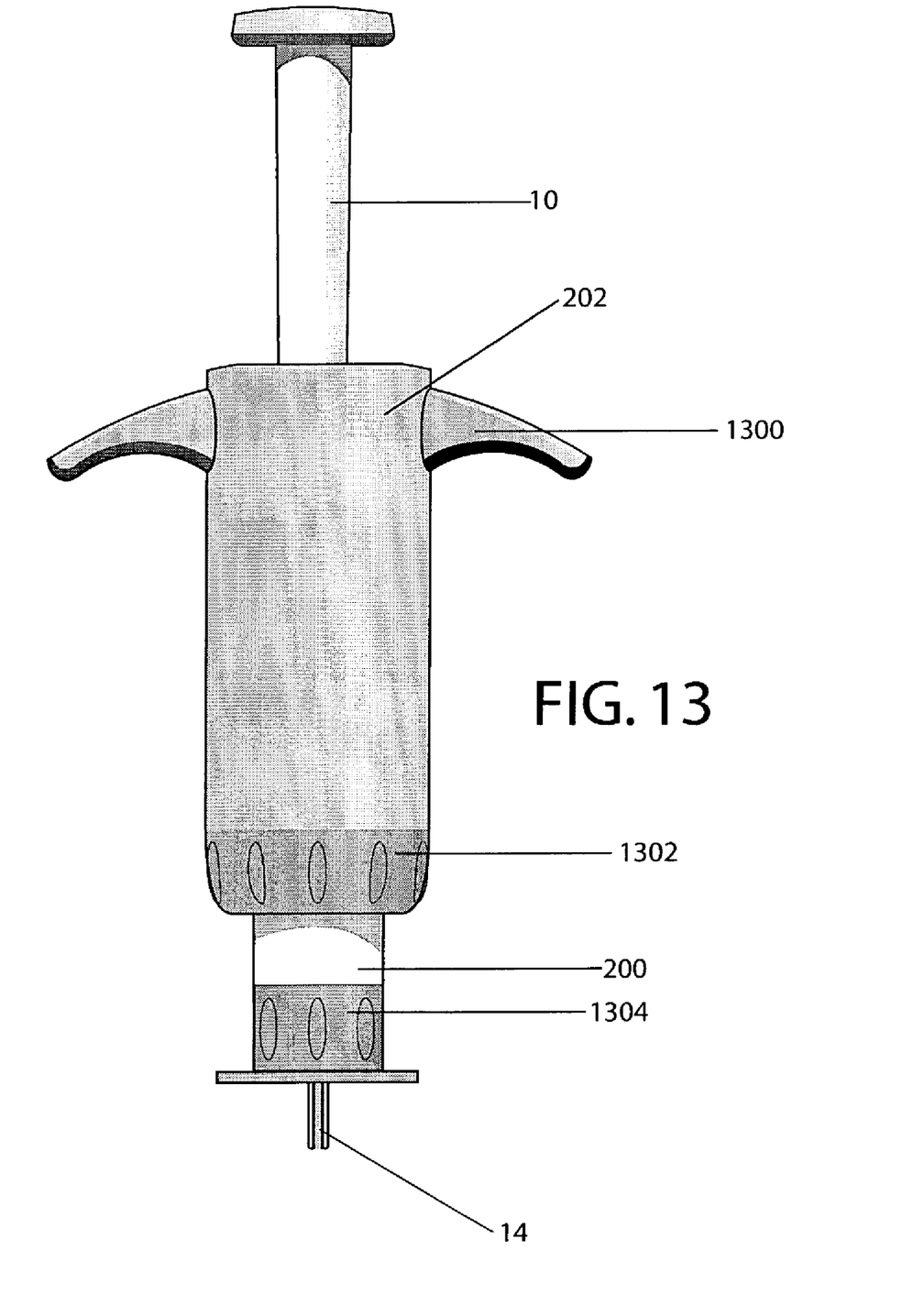
FIG. 13 shows another embodiment of the drug deliver system of the present invention that provides options to further aide the delivery of a drug.

FIG. 13 shows another embodiment of the drug deliver system of the present invention that provides options to further aide the delivery of a drug. In this embodiment, finger grips 1300 comprise two elongated flanges and are connected to the outer housing 202. The finger grips 1300 provide extra support for an end user to grasp when administering a drug. This advantage can be particularly important when rectally delivering a drug to an incapacitated patient, such as one who is undergoing a seizure.

Additionally, to ease the intermediary's efforts in setting the dosage, grips 1302 and 1304 can be located on the distal end of either the inner housing 200 or the outer housing 202, or both. In this embodiment, the grips 1302 and 1304 can be used to help change the relative positions of the inner housing 200 and outer housing 202 as described above in the embodiment of FIG. 4. Or, the grips 1302 and 1304 can be used to rotate the outer housing 202 relative to the inner housing 200 as described above for the embodiment of FIG. 10.

The systems and methods of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:
1. An adjustable dose drug delivery system comprising:
an outer housing;
an inner housing slidably and adjustably disposed within said outer housing and containing an inner housing distal end flange having a hole and located at a distal end;
a syringe containing a syringe tip located at a distal end, and containing a plunger having a stopper at a distal end and a plunger flange at a proximal end, wherein said syringe is fixably disposed within said inner housing, and wherein said syringe tip has a syringe tip aperture for transmitting a dose of a drug, and wherein said plunger is slidably and adjustably disposed on an inner surface of said syringe;
a plunger limiter attached to said outer housing and limiting an axial movement of said plunger flange; and
a locking assembly for adjusting the relative positions of said inner housing and said outer housing.
2. The system of claim 1, wherein the inner housing further comprises a dosage indicator.
3. The system of claim 2, wherein the outer housing further comprises an opening for viewing the dosage indicator.
4. The system of claim 2, wherein the dosage indicator provides a predetermined number of dosages of the drug in increments ranging from approximately 0.25 ml to approximately 10 ml.
5. The system of claim 2, wherein the dosage indicator provides a predetermined number of dosages of the drug in increments ranging from approximately 0.5 mg to approximately 10 mg.
6. The system of claim 1, wherein the outer housing further comprises a dosage indicator.
7. The system of claim 1, further comprising a limiter attached to the inner housing for fixing at least one distance that the plunger can move within the syringe.
8. The system of claim 1, further comprising a limiter attached to the outer housing for fixing at least one distance that the plunger can move within the syringe.
9. The system of claim 1, wherein the plunger is substantially cylindrical in shape.
10. The system of claim 1, further comprising a grip connected to the outer housing.
11. The system of claim 10, wherein the grip is employed to adjust the amount of the dosage of the drug.
12. The system of claim 10, wherein the grip is employed to deliver the dosage to a patient.
13. The system of claim 1, further comprising a grip connected to the inner housing.
14. The system of claim 13, wherein the grip is employed to adjust the amount of the dosage of the drug.
15. The system of claim 13, wherein the grip is employed to deliver the dosage to a patient.
16. The system of claim 1, further comprising a removable covering attached to the syringe.
17. The system of claim 1, wherein the outer housing comprises two portions that are substantially cylindrical in shape.
18. The system of claim 1, further comprising: threadings disposed on the exterior of the inner housing; and threadings disposed on the interior of the outer housing; wherein the threadings on the inner and outer housing are slidably disposed within each other and the relative axial positions of the inner and outer housings are adjustable by rotation of the outer housing relative to the inner housing.
19. The system of claim 18, wherein the threadings on the inner and outer housings are predetermined such that a desired predetermined dosage corresponds to a predetermined amount of rotation of the outer housing relative to the inner housing.
20. The system of claim 1, wherein the drug comprises an anti-seizure medication.
21. The system of claim 20, wherein the anti-seizure medication consists essentially of diazepam.
22. The drug delivery system of claim 1, wherein said syringe tip is disposed within said hole of said inner housing distal end flange and protrudes out of a surface of said inner housing distal end flange.
23. The drug delivery system of claim 1, wherein said syringe tip bidirectionally transmits fluid through said syringe tip aperture.
24. The drug delivery system of claim 1, wherein said plunger limiter contains a plunger limiter aperture through which said plunger slidingly moves.
25. The drug delivery system of claim 1, wherein said drug delivery system is a single use, adjustable dose, drug delivery system.

26. The drug delivery system of claim 25, wherein said drug delivery system is a rectal drug delivery system.

27. A method for adjusting the dosage of a drug, the method comprising the steps of:
providing an outer housing, an inner housing, and a syringe containing a plunger, wherein said inner housing contains an inner housing distal end flange having a hole and located at a distal end, and wherein said syringe contains a syringe tip located at a distal end and a plunger having a stopper at a distal end and a plunger flange at a proximal end, and wherein said syringe tip has a syringe tip aperture for transmitting a dose of a drug, and wherein said plunger is slidably and adjustably disposed on an inner surface of said syringe;
inserting said syringe into said inner housing, wherein said syringe is fixably disposed within said inner housing;
inserting said inner housing into an outer housing having a plunger limiter, wherein said inner housing is slidably and disposed within said outer housing and;
adjusting the relative position of said inner housing and said outer housing;
fixing said relative position of said outer housing to said inner housing; and
restricting the axial motion of said plunger by said plunger limiter.

28. The method of claim 27, wherein the inner housing further comprises a dosage indicator.

29. The method of claim 28, wherein the outer housing further comprises an opening for viewing the dosage indicator.

30. The method of claim 29, further comprising the steps of: connecting a locking assembly to the inner housing and the outer housing for fixing the relative positions of the inner housing and the outer housing; and viewing the dosage indicator through the opening in the outer housing.

31. The method of claim 27, wherein the outer housing further comprises a dosage indicator.

32. The method of claim 27, the method further comprising the step of providing a predetermined number of dosages of the drug in increments ranging from approximately 0.1 ml to approximately 10 ml.

33. The method of claim 27, the method further comprising the step of providing a predetermined number of dosages of the drug in increments ranging from approximately 0.5 mg to approximately 10 mg.

34. The method of claim 27, wherein the method further comprises the step of attaching a limiter to the inner housing for fixing at least one distance that the plunger can move within the syringe.

35. The method of claim 27, wherein the method further comprises the step of attaching a limiter to the outer housing for fixing at least one distance that the plunger can move within the syringe.

36. The method of claim 27, wherein the plunger is substantially cylindrical in shape.

37. The method of claim 27, wherein the method further comprises the step of connecting a grip to the outer housing.

38. The method of claim 37, wherein the method further comprises the step of employing the grip to adjust the amount of the dosage of the drug.

39. The method of claim 37, wherein the method further comprises the step of employing the grip to deliver the dosage to a patient.

40. The method of claim 27, wherein the method further comprises the step of connecting a grip to the inner housing.

41. The method of claim 40, wherein the method further comprises the step of employing the grip to adjust the amount of the dosage of the drug.

42. The method of claim 40, wherein the method further comprises the step of employing the grip to deliver the dosage to a patient.

43. The method of claim 27, wherein the method further comprises the step of attaching a removable covering to the syringe.

44. The method of claim 27, wherein the outer housing comprises two portions that are substantially cylindrical in shape.

45. The method of claim 27, further comprising the steps of: providing threadings disposed on the exterior of the inner housing; providing threadings disposed on the interior of the outer housing; wherein the threadings on the inner and outer housing are slidably disposed within each other; and adjusting the relative axial positions of the inner and outer housings by rotating the outer housing relative to the inner housing.

46. The method of claim 45, wherein the threadings on the inner and outer housings are predetermined such that a desired predetermined dosage corresponds to a predetermined amount of rotation of the outer housing relative to the inner housing.

47. The method of claim 27, wherein the method further comprises the step of attaching a locking assembly to the inner housing and the syringe for fixing the relative positions of the syringe and the inner housing.

48. The method of claim 27, wherein the method further comprises the step of attaching a locking assembly to the inner housing and the outer housing for fixing the relative positions of the inner housing and the outer housing.

49. The method of claim 27, wherein the drug comprises an anti-seizure medication.

50. The method of claim 49, wherein the anti-seizure medication consists essentially of diazepam.

51. The method claim 27, wherein said syringe tip is disposed within said hole of said inner housing distal end flange and protrudes out of a surface of said inner housing distal end flange.

52. The method of claim 27, wherein said syringe tip bidirectionally transmits fluid though said syringe tip aperture.

53. The method of claim 27, wherein said plunger limiter contains a plunger limiter aperture through which said plunger slidingly moves.

* * * * *